(12) United States Patent
Maor et al.

(10) Patent No.: US 6,248,340 B1
(45) Date of Patent: Jun. 19, 2001

(54) SKIN CARE AND PROTECTION COMPOSITION AND A METHOD FOR PREPARATION THEREOF

(75) Inventors: Zeev Maor; Shaul Yehuda, both of Dead Sea (IL)

(73) Assignee: Dead Sea Laboratories, Ltd. (IL)

( * ) Notice: Subject to any disclaimer, the term of this patent is extended or adjusted under 35 U.S.C. 154(b) by 0 days.

(21) Appl. No.: 09/462,642

(22) PCT Filed: Jul. 2, 1998

(86) PCT No.: PCT/IL98/00311

§ 371 Date: Jan. 10, 2000

§ 102(e) Date: Jan. 10, 2000

(87) PCT Pub. No.: WO99/02128

PCT Pub. Date: Jan. 21, 1999

(30) Foreign Application Priority Data

Jul. 10, 1997 (IL) ........................................ 121280

(51) Int. Cl.⁷ ............... A61K 7/42; A61K 7/44; A61K 7/06; A61K 35/78; A61K 33/42
(52) U.S. Cl. ............... 424/401; 424/59; 424/60; 424/74; 424/70.9; 424/195.1; 424/600; 424/661; 424/677; 424/723; 514/844; 514/859; 514/861; 514/863
(58) Field of Search ............... 424/401, 59, 60, 424/74, 70.9, 195.1, 600, 661, 677, 723; 514/844, 859, 861, 863

(56) References Cited

U.S. PATENT DOCUMENTS

| | | | | |
|---|---|---|---|---|
| 5,133,958 | * | 7/1992 | Stuckler | 424/61 |
| 5,679,378 | * | 10/1997 | Fischer | 424/600 |
| 5,849,302 | * | 12/1998 | Safai-Ghomi | 424/195.1 |

FOREIGN PATENT DOCUMENTS

| | | | |
|---|---|---|---|
| 1000950 | * | 5/1989 | (BE) . |
| 08104607 | * | 4/1996 | (JP) . |
| 08231382 | * | 9/1996 | (JP) . |

* cited by examiner

Primary Examiner—Shelly A. Dodson
Assistant Examiner—Marina Lamm
(74) Attorney, Agent, or Firm—Mayer, Brown & Platt

(57) ABSTRACT

The present invention generally relates to a composition useful for care of skin conditions and for skin protection and to a method for its preparation. The present invention further relates to a method for skin care and protection using said composition. More specifically, the present invention relates to a composition combining plant and algae extracts with water solutions from the Dead Sea especially useful for treating skin wrinkles and retaining skin moisture, to a method for the preparation thereof and to a method for skin care and protection comprising application of said composition.

19 Claims, No Drawings

SKIN CARE AND PROTECTION COMPOSITION AND A METHOD FOR PREPARATION THEREOF

FIELD OF THE INVENTION

The present invention generally relates to a composition useful for care of skin conditions and for skin protection and to a method for its preparation. The present invention further relates to a method for skin care and protection using said composition. More specifically, the present invention relates to a composition combining plant and algae extracts with water solutions from the Dead Sea especially useful for treating skin wrinkles and retaining skin moisture, to a method for the preparation thereof and to a method for skin care and protection comprising dermal application of said composition.

BACKGROUND OF THE INVENTION

The skin is the largest organ in the body and serves as a protective barrier from the external environment, impeding the entry of microorganisms, absorption of radiation and loss of water. The skin is composed of three layers differing in their cell types and special functions; an overlaying epithelial layer (epidermis), an underlying connective tissue matrix (dermis) and adipose tissue (hypodermis). Skin roughness is one of the main criteria for assessing the health status of human skin. Changes in ski surface roughness, which give the skin the effect of having wrinkles, may occur due to congenital keratinization disturbances, environmental and job related skin irritations, infectious skin diseases and age related defects. Some skin disorders are related to a specific mineral shortage. About 4–5% of the human body is made up of minerals. It is assumed that specific ions from minerals play an important role in healthy skin metabolism. There are indications that $Mg^{+2}$ is a co factor for phosphate transferring enzymes and participates in cAMP regulation. $Ca^{+2}$ is thought to induce lamellar body secretion and regulate cell membrane permeability and $K^+$ is known to enhance $CO^2$ transport. In some in vitro and in vivo tests magnesium bromide, magnesium chloride, and potassium bromide (all selected Dead Sea salts) exhibited inhibition of skin cell proliferation after dermal application, making them possibly applicable for care of psoriasis (As discussed by Shani, J., Sulliman, A., Katzir, I, and Brener, S. in J. Eur. Acad. Dermratol. Venereol. (1995) 4, 267–272 and by Levi-Shaffer, F., Shani, J., Politi, Y., Rubinichik, E. and Brener, S. in Pharmacology (1996) 52, 321–328). Minerals are capable of restoring moisture due to their hygroscopic characteristics. Minerals, if absorbed into skin cells, may enhance intracellular water capacity. Minerals may be absorbed into the skin from brine, from a bath with dissolved salts, or from application of a mineral rich preparation.

The Dead Sea is the richest natural mineral source in the world, with a concentration of 32% (w/v) dissolved minerals and a unique composition. The main elements found in Dead Sea water are chlorine, magnesium, sodium, calcium, potassium and bromine. For example, the concentration of chlorine in the Dead Sea is 224900 mg/l as opposed to 22900 in the Mediterranean and 19000 in typical ocean water. Magnesium is 44000 mg/l in the Dead Sea as opposed to 1490 and 1350 in the Mediterranean and ocean, respectively. Sodium is 40100 mg/l in the Dead Sea as opposed to 12700 and 10500 in the Mediterranean and ocean, respectively. Calcium is 17200 mg/l in the Dead Sea as opposed to 470 and 400 in the Mediterranean and ocean, respectively. Potassium is 7650 mg/l in the Dead Sea as opposed to 470 and 390 in the Mediterranean and ocean, respectively and bromine is 5300 mg/l in the Dead Sea as opposed to 76 and 65 in the Mediterranean and ocean, respectively.

It has been acknowledged for years that these elements are beneficial for human skin and health. Minerals are alleged to relieve diseases such as rheumatism, acne, eczema and psoriasis (Ma'or, Z., Magdassi, S., Effron, D., Yehuda, S Isr. J. Med. Sci. 32 (suppl 3), 28–35 (1996)). Algae and plants are an especially rich natural source of vitamins and minerals. Algae grown in mineral rich water and in severe environmental conditions are capable of concentrating large amounts of these substances. Uses for algae in food and in external dermal applications, are known, and the use of marine algae in spas is prevalent. There is a large world market for cosmetic compositions containing minerals. However, the benefits of minerals in Dead Sea water are limited due to the natural high concentration of divalent ions and the very high ionic strength of the Dead Sea water. Another drawback of the mineral rich cosmetics marketed today is the fact that the skin itself presents a natural barrier to the penetration of minerals. These drawbacks have a negative effect on the formation and stability of compositions.

The present invention relates to a composition for skin care, especially for care of changes in skin surface roughness (wrinkles), for retaining skin moisture and for relieving skin related diseases such as acne, eczema and psoriasis. The composition of the present invention combines Dead Sea water solutions with algae and plant extracts, achieving a highly mineral rich composition and utilizing the algae bio mass as a carrier of minerals and their possibly controlled release, thereby overcoming the drawbacks of the compositions marketed today and presenting a superior composition for cosmetic use and skin care and protection.

DETAILED DESCRIPTION OF THE INVENTION

The present invention relates to a composition for care of skin conditions, especially changes in skin surface roughness (wrinkles), for retaining skin moisture, and for care of skin related diseases. Skin roughness is one of the main criteria for assessing the health status of human skin. Changes in skin surface roughness, which give the skin the effect of having wrinkles, may occur due to congenital keratinization disturbances, environmental and job related skin irritations (toxic and allergic eczema), infectious skin diseases, UVA and UVB radiation induced skin damages and age related defects. Some skin disorders are related to a specific mineral shortage. About 4–5% of the human body is made up of minerals. It is assumed that specific ions from minerals play an important role in healthy skin metabolism. The composition of the present invention combines Dead Sea water solutions with algae and plant extracts, achieving a highly mineral rich composition, useful for care of skin conditions and for skin protection. Preparation of the composition of the present invention is preferably a two stage process wherein the first step is the preparation of a base comprising:

| | |
|---|---|
| hydrosoluble (HS) Dunaliella extract | 11–11.8% w/w |
| Trigonella foenum extract HS | 4.5–4.7% w/w |
| Zizyphus extract HS | 16.7–17.6% w/w |
| Sclerotium Gum | 0.5–0.6% w/w |
| Methylparaben | 0.075–0.08% w/w |

-continued

| | |
|---|---|
| Propylparaben | 0.0375–0.04% w/w |
| Water | to add up to 100% w/w |

This base is a yellow-orange liquid with the typical characteristics of a pH of about 4.5–6.5, a density (at 20° C.) of about 1.03–1.04, a refractive index (at 20° C.) of about 1.370–1.380 and a water percentage of about 65%. A microbiological analysis showed there to be no aerobic germs or yeasts or molds. The second step is the adding of 10–15% Dead Sea water resulting in the composition of the present invention comprising:

| | |
|---|---|
| hydrosoluble (HS) Dunaliella extract | 10% w/w |
| Trigonella foenum HS extract | 4% w/w |
| Zizyphus HS extract | 15% w/w |
| Dead Sea Water | 10–15% w/w |
| Sclerotium Gum | 0.5% w/w |
| Methylparaben | 0.07% w/w |
| Propylparaben | 0.035% w/w |
| Water | to add up to 100% w/w |

This composition is a yellow-orange liquid with the typical characteristics of a pH between 4.5 to 6.5, a density (at 20° C.) of about 1.00–1.11, a refractive index (at 20° C.) of about 1.39–1.40 and a water percentage of about 64%. A microbiological analysis showed there to be less than 100/g aerobic germs and no yeasts or molds. Dead Sea Water, as defined in the present invention, comprises a clear colorless viscous liquid (at 25° C.) with a specific density of 1.3–1.34 g/ml, pH=4.7–5.3 (at 25° C.), loss on drying (at 120° C.) of 49–50%/w and less than 100 cfu/gr and non pathogenic microbes. The major constituents of the Dead Sea Water referred to in the present invention, as assessed by a water analysis carried out by the Geological Survey of Israel, are:

| | |
|---|---|
| Calcium (Ca+2) | 36000–40000 mg/l |
| Chloride (Cl−) | 320000–370000 mg/l |
| Magnesium (Mg+2) | 90000–95000 mg/l |
| Potassium (K+) | 1300–1500 mg/l |
| Bromide (Br−) | 11000–12000 mg/l |

Algae and plants are an especially rich natural source of vitamins, minerals and other components essential for skin care. The composition of the present invention combines Dead Sea water solutions with algae and plant extracts, achieving a highly mineral rich composition and utilizing the algae bio mass as a carrier of minerals and their release, thereby overcoming the drawbacks of the compositions marketed today and presenting a superior composition for cosmetic use and skin care and protection. The plants used in the composition of the present invention are the *Trigonella foenum* and the Zizyphus tree, preferably the Zizyphus Spina—Christi and the Zizyphus Jujuba. The *Trigonella foenum* is an annual herbaceous plant, from the Fabaceac family, cultivated in the Mediterranean areas. The seeds contain active ingredients, such as mucilage, albumin, lignin, proteins and fatty acids, essential oils, alkaloids, sapegenins, nicotinic and nicotinamide acids, flavenoids vitamins A, B and C and minerals such as calcium, iron and phosphorus in large quantities. A hydrosoluble (HS) extract is achieved by maceration in propylene glycol Codex. The *Trigonella foenum* has been used for centuries in medicine, food and cosmetics. The plant extracts have the capacity of fixing themselves in the skin at the level of the connective tissue where they stay for a long time, acting as a biological dermo-epidermic cellular regenerator. Due to their emollient, firming and regenerative properties, the *Trigonella foenum* extracts are used in cosmetics to treat dry skin. The Zizyphus tree (from the Rhamnaceae family) grows in the Mediterranean areas and in China and India. The tree fruit contains active ingredients such as vitamin C in high concentrations, mucilages, tannins, sugars, pectin, gums, potassium tartrate, magnesium and citric and tartaric acids. Due to the mucilages the fruit extracts have emollient properties and may be used in creams, milks and masks for dry and sensitive skin. A hydrosoluble extract is achieved by maceration in propylene glycol Codex.

The algae preferably used in the composition of the present invention is the Dunaliella (of the order Volvocales), a genus including a variety of unicellular green alga. The Dunaliella demonstrates a remarkable degree of environmental adaptation to salt and is widely distributed in natural habitats and also in habitats of the Dead Sea. This alga has a high contents of glycerol, β carotene, vitamins such as thiamin, pyridoxine, riboflavin, tocoperol and biotin, and also contains substances found to posses anti cancer activity in the skin. Sclerotium Gum (Amigel), optionally used in the composition of the present invention, is a polysaccharide gum produced by the bacteria *Sclerotium rolfssii*, composed of glucose monomers. It has gelling and thickening characteristics being able to form a gel without being neutralized and shows a good stability. Also optionally used in the present invention are preservatives, such as methylparaben, propylparaben, imidazolidinyl urea and bronopol, emulsifiers and co emulsifiers such as PEG-40 (polyethylene glycol) stearate, sorbitan tristearate and glyceryl steatrate, emolients such as cetyl alcohol, octyl palmitate and hexyl laurate and sunscreens such as octyl methoxycinnamate. Perfumes may be added to the composition, such as elixia perfume. Solvents, other than water, may be used, such as propylene glycol.

The said invention will be further illustrated by the following experiments. These experiments do not intend to limit the scope of the invention but to demonstrate and clarify it only.

Experiment 1—Effect of the Composition on Skin Roughness, Detected by Computer Aided Laser Profilometry of the Skin Surface An accurately registering the roughness of the skin's surface contact free process was developed utilizing computer aided laser profilometry for quantitative analysis of the skin's surface structure. To rule out measuring errors caused by body movements, evaluation is performed on silicon based skin impressions. 20 women (subjects) aged between 22 and 63 applied the composition of the present invention. 3% and 5% compositions and a placebo (described in the following section) were applied in three different test groups twice a day for a period of 4 weeks. Measurements were taken from the right and left forearm, crossover and randomized at the beginning and end of the application period. The impressions were taken from strictly the same areas of skin. Twelve hours before the silicon impression was taken, the subjects were not allowed to apply cream to the tested skin area or to clean it with active washing substances. The subjects were acclimatized to the measuring room temperature for 30 minutes before the measurements were taken. The structural changes of the epidermis are quantitatively classified, in the method of the experiment, on the basis of various surface measurement values normed in accordance with German Industrial Standards (DIN) and International Standards Organization (ISO).

Control group (placebo)

A placebo cream was prepared by:

(the ingredients are mentioned by their INCI (International Nomenclature Cosmetics Ingredients) names)

| A. Water phase (mixing at 75° C.) | water | 75.16% |
|---|---|---|
| | methylparaben | 0.3% |
| | imidazolidinyl urea | 0.2% |
| | bronopol | 0.04% |
| | propylene glycol | 2% |
| | PEG-40 stearate | 1.2% |
| B. Oily phase (mixing at 75° C.) | | |
| | glycerol stearate | 4% |
| | cetyl alcohol | 3% |
| | sorbitan tristearate | 0.8% |
| | propylparaben | 0.2% |
| | octyl methoxycinnamate | 1% |
| | octyl palmitate | 6% |
| | hexyl laurate | 6% | adding B to A homogenizing for 10 minutes (at 75° C.), cooling to 45° C. and adding:

perfumes 0.1% bringing the pH to 5.5+1.0 and cooling to room temperature.

The arithmetical mean of the individual roughness depths of five adjacent measured distances of identical length of the (digitally) filtered profile (Rz) was measured for the subjects as explained above. The results were that the roughness parameter Rz determined in accordance with the DIN norm improved in relative terms by 24.9% on the average. The values varied among the subjects between 10.9% and 35.1% in the relative terms. This skin enhancing effect is greater than the effect with "basic" medical creams, which have been used in dermatology for years to improve skin structure, which achieve values of up to 10–15%.

3% Composition Group

For preparing a 3% composition 2.55% of the base of step 1 of the present invention and 0.45% Dead Sea water were mixed together and were added to the placebo at 35° C. This composition was applied to the subjects as above and the Rz parameter was calculated as above. The results show that the roughness parameter Rz determined in accordance with the DIN norm improved in relative terms by 25.6% on the average. The values varied among the subjects between 14.1% and 39.1% in the relative terms, greater than the effect with "basic" medical creams, as mentioned above.

5% Composition Group

For preparing a 5% composition 4.25% of the base of step 1 of the present invention and 0.75% Dead Sea water were mixed together and were added to the placebo at 35° C. This composition was applied to the subjects as above and the Rz parameter was calculated as above. The results show that the roughness parameter Rz determined in accordance with the DIN norm improved in relative terms by 43.2% on the average. The values varied among the subjects between 28.5% and 49.5% in the relative terms, much greater than the effect with "basic" medical creams, or the placebo or the 3% composition as mentioned above. Up to a 12% composition may be used with very good results. Thus, the compositions of the present invention permits the care of normal and dry skin with a very high effect on skin roughness.

Experiment 2—Effect of Composition on Skin Moisture as Detected by Corneometer

The skin moisture of the outer layer of the epidermis (stratum corneum) is determined by capacitance measurement with the corneometer. The corneometer is based on the different dielectric constants of water and other substances. An appropriately formed measuring capacitor responds to the samples inserted into its measuring body with differing capacitance changes which are registered and evaluated automatically by the device. The active probe of the device is pressed onto the area of skin tested and the degree of moisture on the skin's surface is displayed. Thus, the device can indicate the changes in moisture of the skins surface after and before treatment etc. 20 woman (subjects) aged between 22 and 58 applied the composition of the present invention. 3% and 5% compositions and a placebo were applied in three different test. Measurements were taken from three different places in the lower arm and a mean of the values obtained was calculated. The measurements were taken initially after application, after 8 hours and after 12 hours. The untreated skin of the contralateral lower arm was used for control measurements. The subjects were acclimatized to a temperature of 22° C. and 60% relative humidity for 45 minutes before the measurements were taken.

Only subjects with no pathological changes on either lower arm were included in this experiment. In none of the subjects did any irritations occur on the lower arm during the application period. The results for the placebo group were that there was a statistically significant improvement in skin moisture of 8.2% after 8 hours and of 6.2% after 12 hours. A 3% composition, as described in experiment 1 was prepared and applied to the subjects. The results for the 3% composition group were that there was a statistically significant improvement in skin moisture of 9.4% after 8 hours and of 6.9% after 12 hours. A 5% composition, as described in experiment 1 was prepared and applied to the subjects. The results for the 5% composition group were that there was a statistically significant improvement in skin moisture of 10.8% after 8 hours and of 7.4% after 12 hours. Up to a 12% composition may be used with very good results. Thus, the effect on skin moisture of the composition of the present invention can be described as very good.

What is claimed is:

1. A liquid composition useful for skin care and protection comprising Dead Sea water, hydrosoluble algae extracts and hydrosoluble plant extracts.

2. A composition according to claim 1 wherein the algae is of the genus Dunaliella.

3. A composition according to claim 1 wherein the plant extracts are derived from *Trigonella foenum* and *Zizyphus*.

4. A composition according to claim 1 wherein the composition further comprises a polysaccharide as a gelling component.

5. A composition according to claim 4 wherein the polysaccharide is Sclerotium Gum.

6. A composition according to claim 1 wherein the composition further comprises preservatives.

7. A composition according to claim 6 wherein the preservatives are selected from the group consisting of methylparaben and propylparaben, imidazolidinyl urea and bronopol.

8. A composition according to claim 1 wherein the composition contains approximately 10% w/w Dunaliella HS extract, approximately 4% w/w *Trigonella foenum* HS extract, approximately 15% w/w *Zizyphus* HS extract, 10–15% w/w Dead Sea water, approximately 0.5% w/w Sclerotium Gum, approximately 0.07% w/w methylparaben, approximately 0.035% w/w propylparaben and water to complete up to 100% w/w.

9. A composition according to claim 1 wherein the composition further contains at least one of emulsifiers, co emulsifiers, emolients, sunscreens and perfumes.

10. A composition according to claim 9 wherein the emulsifiers are selected from the group consisting of PEG-40 stearate and sorbitan tristearate, the co emulsifiers are glyceryl steatrate, the emolients are selected from the group consisting of cetyl alcohol, octyl palmitate and hexyl laurate, the sunscreen is octyl methoxycinnamate, and the perfume is elixia perfume.

11. A method for the preparation of a liquid skin care and protection composition comprising preparing an algae and plant extract base and successively adding Dead Sea water.

12. A method according to claim 11 wherein the algae is of the genus Dunaliella, and the plant extracts are derived from *Trigonella foenum* and Zizyphus.

13. A method according to claim 11 wherein the base further comprises polysaccharides and preservatives.

14. A method according to claim 13 wherein the polysaccharide is Sclerotium Gum, and the preservatives are selected from the group consisting of methylparaben and propylparaben, imidazolidinyl urea and bronopol.

15. A method according to claim 11 further comprising:

mixing water, methylparaben, imidazolidinyl urea, bronopol, propylene glycol and PEG-40 stearate at approximately 75° C., mixing glycerol stearate, cetyl alcohol, sorbitan tristearate, propylparaben, octyl methoxycinnamate, octyl palmitate, hexyl laurate at approximately 75° C., homogenizing for 10 minutes at 75° C., cooling to 45° C., adding perfume, adding an algae and plant extract base and Dead Sea water, bringing the mixture to pH 5.5+1.0 and cooling to room temperature.

16. A method according to claim 15 wherein the base and Dead Sea water comprise up to 12% of the composition.

17. A composition according to claim 1 wherein skin care and protection are care of skin surface roughness (wrinkles), retaining skin moisture, and care of skin related diseases.

18. A composition according to claim 17 wherein the skin related diseases are acne, eczema and psoriasis.

19. A method for skin care and protection comprising the steps of:

applying to the skin an amount of a liquid composition comprising Dead Sea water, hydrosoluble algae extracts and hydrosoluble plant extracts.

* * * * *